United States Patent [19]
Minisci et al.

[11] Patent Number: 5,763,624
[45] Date of Patent: Jun. 9, 1998

[54] PROCESS FOR THE SYNTHESIS OF 1-PYRIDINIUMPROPANE-3-SULPHONATE

[75] Inventors: Francesco Minisci; Francesca Fontana; Anna Serri, all of Milan; Roberto Baima, Novara, all of Italy

[73] Assignee: Galvanevet S.p.A., Novara, Italy

[21] Appl. No.: 658,180

[22] Filed: Jun. 4, 1996

[30] Foreign Application Priority Data

Jun. 8, 1995 [IT] Italy ................. MI95A12089

[51] Int. Cl.$^6$ ............. C07D 213/34; C07D 213/20
[52] U.S. Cl. ........................... 546/339; 546/347
[58] Field of Search ........................ 546/339, 347

[56] References Cited

U.S. PATENT DOCUMENTS

| | | | |
|---|---|---|---|
| 4,148,797 | 4/1979 | Pluss et al. | 546/344 |
| 4,430,180 | 2/1984 | Lemke et al. | 204/48 |
| 4,837,330 | 6/1989 | Braun et al. | 546/339 |
| 5,424,438 | 6/1995 | Chitofratti et al. | 546/336 |
| 5,512,679 | 4/1996 | Meier et al. | 546/339 |

*Primary Examiner*—Alan L. Rotman
*Attorney, Agent, or Firm*—Young & Thompson

[57] ABSTRACT

1-pyridiniumpropane-3-sulphonate is obtained by reacting 1-allylpyridinium chloride (3) and alkaline bisulfite, in an aqueous solution, in the presence of radical initiators, such as oxygen, hydrogen peroxide, peroxides, alkylhydroperoxides and alkaline or ammonium persulfates.

7 Claims, No Drawings

PROCESS FOR THE SYNTHESIS OF 1-PYRIDINIUMPROPANE-3-SULPHONATE

BACKGROUND OF THE INVENTION

The present invention concerns a new and advantageous synthesis process for preparing 1-pyridiniumpropane-3-sulphonate. 1-pyridinium-3-sulphonate (PPS) is a compound represented by the formula (1):

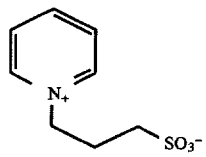

(1)

It is a dipolar ion—or, more commonly called, a zwitterion-widely used in preparing electrolytic baths.

PPS is generally synthesized in two steps. In the first step, one starts from allylalcohol and bisulfite, to obtain propanesultone (2) being used as an intermediate:

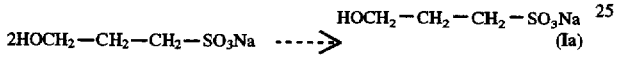

In the second step, sultone (2) is caused to react with pyridine to obtain the final product (1):

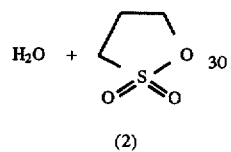

This synthesis, adopted at present, involves however different drawbacks. To start with—as reported for example by G. E. Milo and E. C. Castro, in Cancer Letters, Vol. 31 (1986), page 1—the propanesultone (2) obtained in the first step is a cancerous substance. Its use is thus subject to a series of precautions and special procedures, such as to make its replacement by less harmful reactants and/or intermediates highly desirable.

A further drawback of the known process lies in the fact that the synthesis—in step Ia—of sultone (2) is technologically very complex, in that it requires a vacuum distillation at a pressure between 127 and 254 pa (1-2 torr), with all the practical problems connected with the creation and maintenance of such a high vacuum.

SUMMARY OF THE INVENTION

The object of the present invention is to thus conceive a process for preparing 1-pyridiniumpropane-3-sulphonate, which requires no vacuum steps, which employs no toxic or anyhow harmful intermediates, and which simultaneously allows to obtain high reaction yields.

Said object is reached, with the present invention, by a process for the synthesis of 1-pyridiniumpropane-3-sulphonate, characterized in that said 1-pyridiniumpropane-3-sulphonate is obtained by reacting 1-allylpyridinium chloride and alkaline bisulfite, in an aqueous solution, in the presence of radical initiators.

Said radical initiators are suitably selected from the group consisting of oxygen, hydrogen peroxide, peroxides, alkylhydroperoxides and alkaline or ammonium persulfates.

preferably, the reaction temperature is between 20° C. and the reflux temperature. The reaction is generally carried out with a 1 to 3 mole ratio between the alkaline bisulfite and the 1-allylpyridinium chloride, and the initiator represents 1 to 20% in moles of the 1-allylpiridinium chloride.

The 1-allylpyridinium chloride (3), which acts as precursor for the process of the present invention, can be easily synthesized—as known—in a reaction step previous to the actual process, starting from a mixture of pyridine and allyl chloride, by simple heating between 30 and 100° C.:

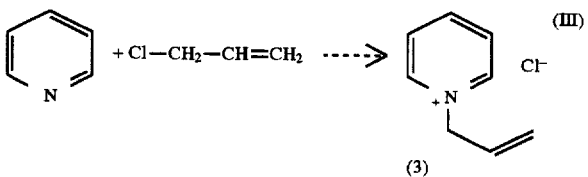

DESCRIPTION OF THE PREFERRED EMBODIMENT

According to the invention, the 1-allylpyridinium chloride, however obtained, is dissolved into an aqueous solution and alkaline bisulfite is added thereto. The radical initiator, in catalytic amounts, is then added drop by drop under stirring, while the reaction takes place. If gaseous oxygen or gaseous air are used as initiators, they can be bubbled in the solution for the whole time of the reaction. The pH of the solution is adjusted between 6 and 8, for instance with NaOH. The reaction is carried out, as seen above, at a temperature between 20° C. and the reflux temperature, according to the following scheme:

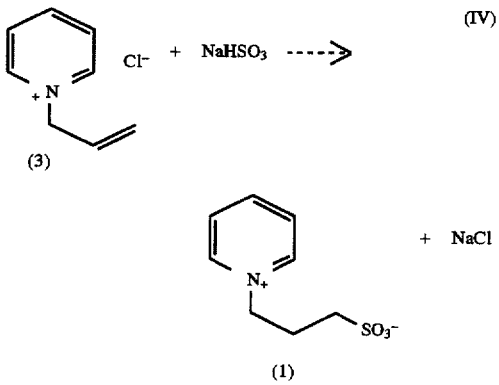

The PPS obtained through the reaction (IV) can then be isolated in different ways from the mixture of salts formed at the end of the reaction. A specially convenient method, which leads to a particularly pure product, consists in carrying out the selective extraction by means of organic solvents, for instance acetic acid. Use can also be made of mixtures of organic solvents with water. As an alternative, the separation can be carried out using ion exchange resins.

The present invention is now described in further detail, with reference to some non-limiting examples.

EXAMPLE 1

A solution was prepared, containing 0.1 moles of 1-allylpyridinium chloride, 0.2 moles of sodium bisulfite and 0.1 moles of NaOH, in 130 cm$^3$ of water. To said solution there were added within 90 minutes, 0.01 moles of $Na_2S_2O_8$, dissolved into 10 cm$^3$ of water, at a temperature of 60° C. The solution was refluxed for 30 minutes; it was then cooled down to 60° C., and 0.01 moles of $Na_2S_2O_8$ were again added thereto within one hour. The solution was subsequently dried up and the residue analysed by NMR, by comparison with a sample of 1-pyridiniumpropane-3-sulphonate; equal results were obtained. The $CH_2$ in position 2 showed a quintet with β 2.46, the $CH_2$ in position 3 showed a triplet with δ 4.78, two hydrogens were in position δ and showed a triplet with β 8.08, an aromatic hydrogen in position Γ showed a triplet with δ 8.56, and two aromatic hydrogens in position α showed a doublet with α 8.90. The analysis evidenced a yield of 92%, with total conversion of the reagents.

EXAMPLE 2

The reaction was carried out exactly as in Example 1, except that the 0.01 moles of radical initiator $Na_2S_2O_8$, at 60° C., were added only once, within four hours. An 82% yield was obtained.

EXAMPLE 3

The reaction was carried out as in Example 2, except that there were added 0.4 moles of sodium bisulfite and 0.2 moles of NaOH, and that the radical initiator consisted of 0.01 moles of 5% hydrogen peroxide, added under stirring within four hours. A 74% yield was obtained.

EXAMPLE 4

The reaction was carried out as in Example 3, except that the radical initiator, instead of hydrogen peroxide, consisted of 0.01 moles of tert-butyl hydroperoxide. A 60% yield was obtained.

EXAMPLE 5

The reaction was carried out as in Example 3, but in the absence of hydrogen peroxide, the radical initiator consisting of a strong airflow bubbled into the reaction solution. A 38% yield was obtained.

As it appears evident from the above description and from the previous examples, the present invention allows to synthesize—with yields even higher than those obtained with the present industrial process-1-pyridiniumpropane-3-sulphonate, without having to resort to a harmful intermediate such as sultone (2), and hence simultaneously avoiding also the technological difficulties involved in its preparation. The process of the present invention thus turns out to be extremely simple, it requires no particularly expensive equipment to carry out the same, it allows to obtain very high yields and, in the event of a separation by selective extraction, it leads to an extremely pure product.

What is claim is:

1. Process for synthesizing 1-pyridiniumpropane-3-sulphonate, comprising reacting 1-allylpyridinium chloride and alkaline bisulfite in an aqueous solution at a temperature from about 20° C. to reflux temperature of said solution, in the presence of a radical initiator selected from the group consisting of alkaline persulfate, ammonium persulfate, oxygen, and hydrogen peroxide.

2. The process of claim 1, wherein said alkaline bisulfite and said 1-allylpyridinium chloride are present in a mole ratio ranging 1:1 to 3:1.

3. The process of claim 1, wherein said radical initiator is present in an amount of 1–20 mole percent based on said 1-allylpyridinium chloride.

4. The process of claim 1, further comprising, subsequent to said reacting step, contacting said aqueous solution with at least one organic solvent or a mixture of at least one organic solvent and water, thereby selectively to extract said 1-pyridiniumpropane-3-sulphonate from said aqueous solution.

5. The process of claim 4, wherein said at least one organic solvent is acetic acid.

6. The process of claim 1, further comprising separating said 1-pyridiniumpropane-3-sulphonate from said aqueous solution using an ion exchange resin.

7. Process for synthesizing 1-pyridiniumpropane3-sulphonate, comprising the following steps:

a) heating a mixture of pyridine and allyl chloride at a temperature between 30° C. and 100° C.; and b) reacting 1-allylpyridinium chloride resulting from step a) above, with alkaline bisulfite in an aqueous solution at a temperature from about 20° C. to reflux temperature of said solution, in the presence of a radical initiator selected from the group consisting of alkaline persulfate, ammonium persulfate, oxygen, and hydrogen peroxide.

* * * * *

UNITED STATES PATENT AND TRADEMARK OFFICE
CERTIFICATE OF CORRECTION

PATENT NO. : 5,763,624
DATED : June 9, 1998
INVENTOR(S) : Francesco MINISCI et al.

It is certified that error appears in the above-indentified patent and that said Letters Patent is hereby corrected as shown below:

On the title page, Item [30], change the identification of the Italian priority document from "MI95A12089" to --MI95A1208--.

Signed and Sealed this

Ninth Day of February, 1999

Attest:

Attesting Officer

Acting Commissioner of Patents and Trademarks